(12) United States Patent
Erdemir et al.

(10) Patent No.: US 10,799,188 B2
(45) Date of Patent: Oct. 13, 2020

(54) SYSTEM AND METHOD FOR REAL-TIME ELECTROPHYSIOLOGICAL MAPPING

(71) Applicant: St. Jude Medical, Cardiology Division, Inc., St. Paul, MN (US)

(72) Inventors: Erhan Erdemir, Maplewood, MN (US); Wenwen Li, San Jose, CA (US); Carlo Pappone, Cernusco Lombardone (IT)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 90 days.

(21) Appl. No.: 16/185,935

(22) Filed: Nov. 9, 2018

(65) Prior Publication Data
US 2019/0150855 A1     May 23, 2019

Related U.S. Application Data

(62) Division of application No. 15/148,009, filed on May 6, 2016, now Pat. No. 10,238,350.

(60) Provisional application No. 62/158,578, filed on May 8, 2015.

(51) Int. Cl.
*A61B 5/00*       (2006.01)
*A61B 5/042*     (2006.01)
(Continued)

(52) U.S. Cl.
CPC .............. *A61B 5/743* (2013.01); *A61B 5/044* (2013.01); *A61B 5/046* (2013.01); *A61B 5/0422* (2013.01);
(Continued)

(58) Field of Classification Search
CPC ............................. A61B 5/743; A61B 5/0422
(Continued)

(56) References Cited

U.S. PATENT DOCUMENTS 5,697,377 A    12/1997   Wittkampf
5,983,126 A    11/1999   Wittkampf
(Continued)

FOREIGN PATENT DOCUMENTS

JP       2007117746       5/2007
JP       2014502556       2/2014
(Continued)

*Primary Examiner* — Nadia A Mahmood
(74) *Attorney, Agent, or Firm* — Wiley Rein LLP

(57) ABSTRACT

A method of generating a real-time electrophysiology map, such as a cardiac electrophysiology map, includes displaying a cardiac surface model and receiving a plurality of electrophysiology data points (e.g., using a plurality of intracardiac electrodes). The electrophysiology data from the received electrophysiology data points can be displayed and updated on the cardiac surface model in real-time when it satisfies a preset inclusion criteria, such as a projection distance criterion (e.g., the electrophysiology data point is within a preset distance of the cardiac surface model), a contact force criterion (e.g., the intracardiac catheter is exerting at least a preset contact force on the tissue surface), and/or an electrical coupling criterion (e.g., the electrode-tissue electrical coupling exceeds a preset threshold). New electrophysiology data points can be received when a triggering event, such as a point in the cardiac cycle, occurs, or according to a preset timer interval.

17 Claims, 9 Drawing Sheets

(51) Int. Cl.
*A61B 5/046* (2006.01)
*A61B 5/044* (2006.01)

(52) U.S. Cl.
CPC .......... *A61B 5/6859* (2013.01); *A61B 5/7207* (2013.01); *A61B 5/7285* (2013.01)

(58) Field of Classification Search
USPC ........................................................ 600/523
See application file for complete search history.

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 2007/0073179 A1 | 3/2007 | Afonso et al. |
| 2009/0262979 A1 | 10/2009 | Markowitz et al. |
| 2012/0029504 A1 | 2/2012 | Afonso et al. |
| 2014/0330150 A1 | 11/2014 | Thakur et al. |
| 2015/0057507 A1* | 2/2015 | Koyrakh .............. A61B 5/0402 600/301 |
| 2016/0120427 A1 | 5/2016 | Zino et al. |

FOREIGN PATENT DOCUMENTS

| | | |
|---|---|---|
| JP | 2014506171 | 3/2014 |
| WO | 2007035306 | 3/2007 |

\* cited by examiner

SYSTEM AND METHOD FOR REAL-TIME ELECTROPHYSIOLOGICAL MAPPING

CROSS-REFERENCE TO RELATED APPLICATIONS

This application is a divisional of U.S. application Ser. No. 15/148,009, filed 6 May 2016 ("the '009 application"), which claims the benefit of U.S. provisional application No. 62/158,578, filed 8 May 2015 ("the '578 application"). The '009 and '578 applications are hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for generating an electrophysiology map from data collected by a roving electrophysiology probe. Even more specifically, the instant disclosure relates to the creation and display of such electrophysiology maps in real time.

Electrophysiological mapping, and more particularly electrocardiographic mapping, is a part of numerous cardiac diagnostic and therapeutic procedures. As the complexity of such procedures increases, however, it is desirable to more rapidly provide electrophysiology data to practitioners, including providing such data in real time.

BRIEF SUMMARY

Disclosed herein is a method of generating a real-time electrophysiology map of a portion of a patient's heart, including the steps of: displaying a model of a surface of the portion of the patient's heart; receiving a plurality of electrophysiology data points using a plurality of intracardiac electrodes, each electrophysiology data point of the plurality of electrophysiology data points including measured electrophysiology data and measured location data; and, for each received electrophysiology data point of the plurality of received electrophysiology data points: determining a distance from the measured location data to the surface of the portion of the patient's heart; and graphically representing the measured electrophysiology data on the model of the surface of the portion of the patient's heart in real-time when the distance from the measured location data to the surface of the portion of the patient's heart falls below a preset projection threshold.

To update the electrophysiology map in real time, it is contemplated to repeat: receiving a plurality of electrophysiology data points using a plurality of intracardiac electrodes; determining a distance from the measured location data to the surface of the portion of the patient's heart for each received electrophysiology data point of the plurality of received electrophysiology data points; and graphically representing the measured electrophysiology data on the model of the surface of the patient's heart in real-time for each received electrophysiology data point of the plurality of received electrophysiology data points according to a preset time interval. The preset time interval can be user-selectable.

In other embodiments, these steps are repeated when a preset triggering event occurs. The preset triggering event can be a point in the cardiac cycle. It can also be a user-selectable event.

In certain aspects of the disclosure, only measured electrophysiology data from a current time interval or triggering event is graphically represented on the model of the surface of the portion of the patient's heart.

In some embodiments, one or more received electrophysiology data points of the plurality of received electrophysiology data points can be saved, for example in response to a user command to save the one or more received electrophysiology data points and/or when the distance from the measured location data for the one or more received electrophysiology data points to the surface of the patient's heart falls below the preset projection threshold.

Not only can real-time electrophysiology data be displayed as described above, but the method can also include graphically representing a plurality of saved electrophysiology data points on the model of the surface of the portion of the patient's heart. The graphical representation of the measured electrophysiology data and that of the saved electrophysiology data can respectively use first and second display conventions, which can be different from each other.

Further, it is contemplated that at least one received electrophysiology data point of the plurality of received electrophysiology data points can be saved to the plurality of saved electrophysiology data points when the distance from the measured location data for the one or more received electrophysiology data points to the surface of the patient's heart falls below the preset projection threshold. The at least one received electrophysiology data point so saved can be used to update and/or overwrite electrophysiology data for at least one previously-saved electrophysiology data point having common location data to the measured location data for the at least one received electrophysiology data point.

In another embodiment disclosed herein, a system for generating a real-time electrophysiology map of a portion of a patient's heart includes: a surface modeling processor configured to display a model of a surface of the portion of the patient's heart; and an electrophysiology mapping processor configured to: receive, as input, a plurality of electrophysiology data points, each electrophysiology data point of the plurality of electrophysiology data points including measured electrophysiology data and measured location data; display, in real-time on the model of the surface of the patient's heart, the measured electrophysiology data for each electrophysiology data point of the plurality of electrophysiology data points where a distance between the measured location data for the electrophysiology data point to the surface of the patient's heart falls below a preset projection threshold.

The electrophysiology mapping processor can also be configured to save one or more electrophysiology data points of the plurality of electrophysiology data points to a plurality of saved electrophysiology data points. For example, the electrophysiology mapping processor can be configured to update and/or overwrite one or more previously-saved electrophysiology data points when saving the one or more electrophysiology data points to the plurality of saved electrophysiology data points.

In addition, the electrophysiology mapping processor can be configured to display a plurality of saved electrophysiology data points on the model of the surface of the patient's heart.

Also disclosed herein is a method of generating a real-time electrophysiology map of a portion of a patient's heart, including: displaying a model of a surface of the portion of the patient's heart; detecting a cardiac triggering event, and, upon detecting the cardiac triggering event: receiving a plurality of electrophysiology data points using a plurality of intracardiac electrodes, each electrophysiology data point of the plurality of electrophysiology data points including measured electrophysiology data and measured location data; and graphically representing, on the model of the surface of the portion of the patient's heart in real-time, the measured electrophysiology data for each electrophysiology data point of the plurality of electrophysiology data points that meets at least one preset inclusion criterion. The preset inclusion criterion can be a projection distance criterion, a contact force criterion, an electrical coupling criterion, and/or a cycle length criterion. The method can optionally include removing measured electrophysiology data from any prior triggering event from the model of the surface of the portion of the patient's heart before graphically representing the measured electrophysiology data for such electrophysiology data point on the model of the surface of the portion of the patient's heart.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses, and systems for the creation of electrophysiology maps (e.g., electrocardiographic maps) in real-time. For purposes of illustration, several exemplary embodiments will be described in detail herein in the context of a cardiac electrophysiology procedure, where such real-time electrophysiology maps can be useful to show changes in cardiac electrophysiology during mapping, pacing, ablation, or otherwise. It is contemplated, however, that the methods, apparatuses, and systems described herein can be utilized in other contexts.

Figure 1:
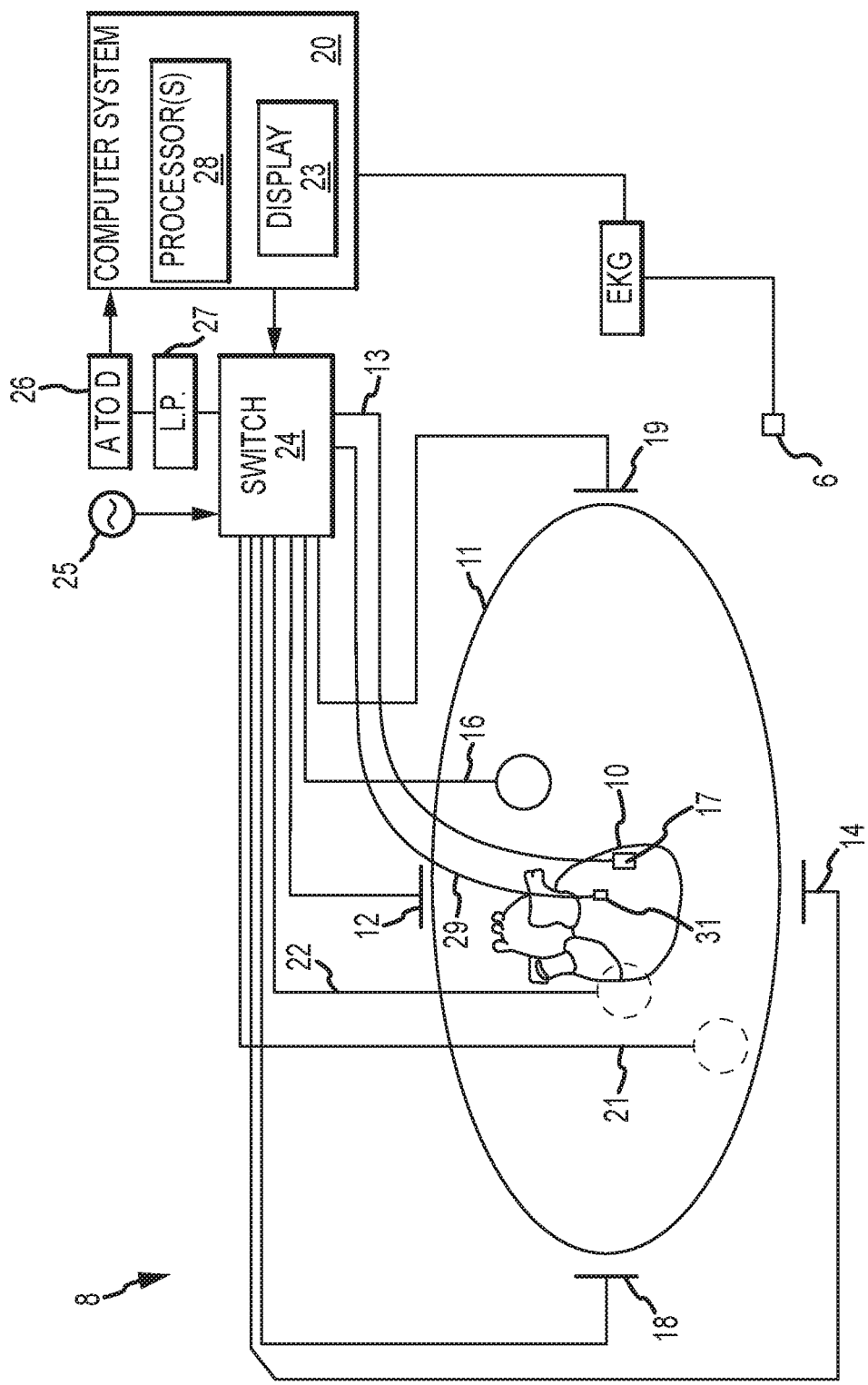
FIG. 1 is a schematic diagram of a localization system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the measured electrical activity. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference. This process can be referred to as "localization" of those objects.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, such as, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along the sternum and spine of the patient in the thorax region, and may be referred to as the Chest and Back electrodes. The z-axis electrodes 16, 22 are applied along a third axis generally orthogonal to both the x-axis and the y-axis, such as along the inner thigh and neck regions of the patient, and may be referred to as the Left Leg and Neck electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional surface electrocardiogram ("ECG" or "EKG") system leads in place. In certain embodiments, for example, a standard set of 12 ECG leads may be utilized for sensing electrocardiograms of the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion. This representative catheter electrode 17 can be referred to as a "roving electrode," "moving electrode," or "measurement electrode." Typically, multiple electrodes on catheter 13, or on multiple such catheters, will be used. In one embodiment, for example, system 8 may utilize sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
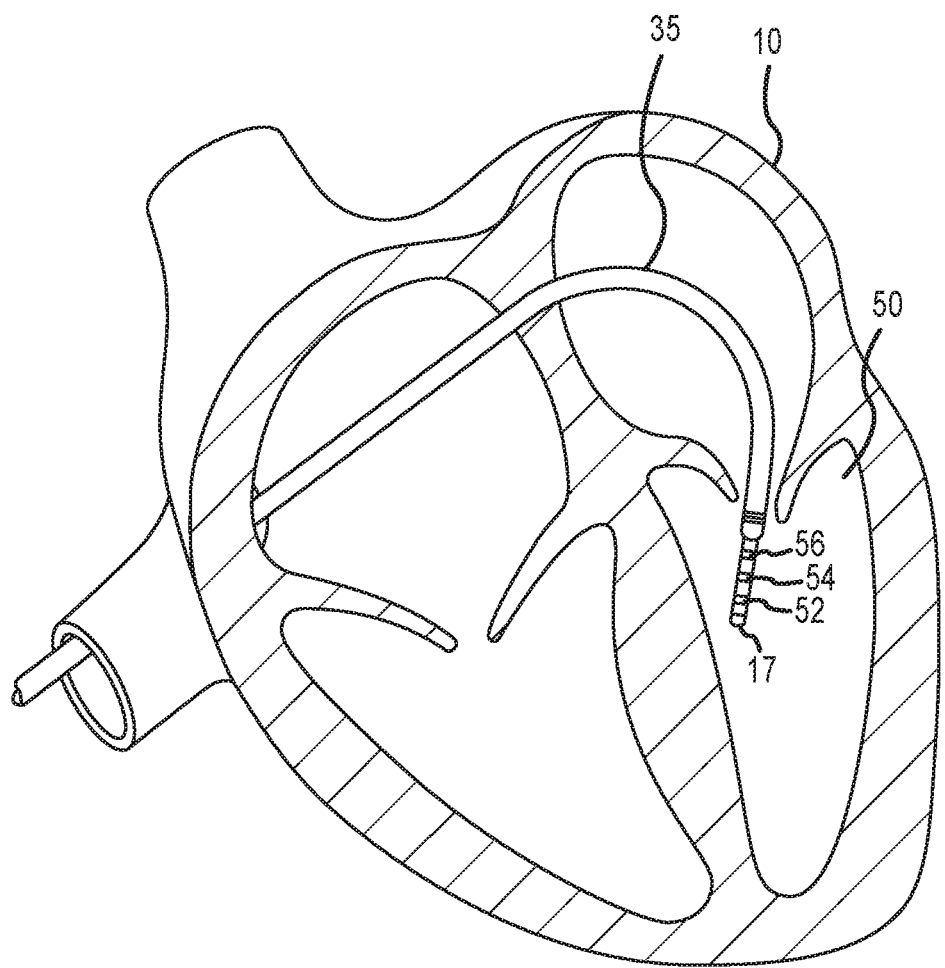
FIG. 2 depicts an exemplary catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the measurement electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The measurement electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the measurement electrodes 17, 52, 54, 56 within heart 10.

The measured voltages may be used by system 8 to determine the location in three-dimensional space of the electrodes inside the heart, such as measurement electrodes 17, 52, 54, 56, relative to a reference location, such as reference electrode 31. That is, the voltages measured at reference electrode 31 may be used to define the origin of a coordinate system, while the voltages measured at measurement electrodes 17, 52, 54, 56 may be used to express the location of measurement electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as MediGuide™ Technology and the EnSite Precision™ system, both from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

In general, electrophysiology maps are created from a plurality of electrophysiology data points, each of which includes both measured electrophysiology data (e.g., cardiac electrograms ("EGMs")) and location data (e.g., information regarding the location of catheter 13 and/or the electrodes thereon), allowing the measured electrophysiology information to be associated with a particular location in space (that is, allowing the measured electrophysiology information to be interpreted as indicative of electrical activity at a point on the patient's heart).

Figure 3:
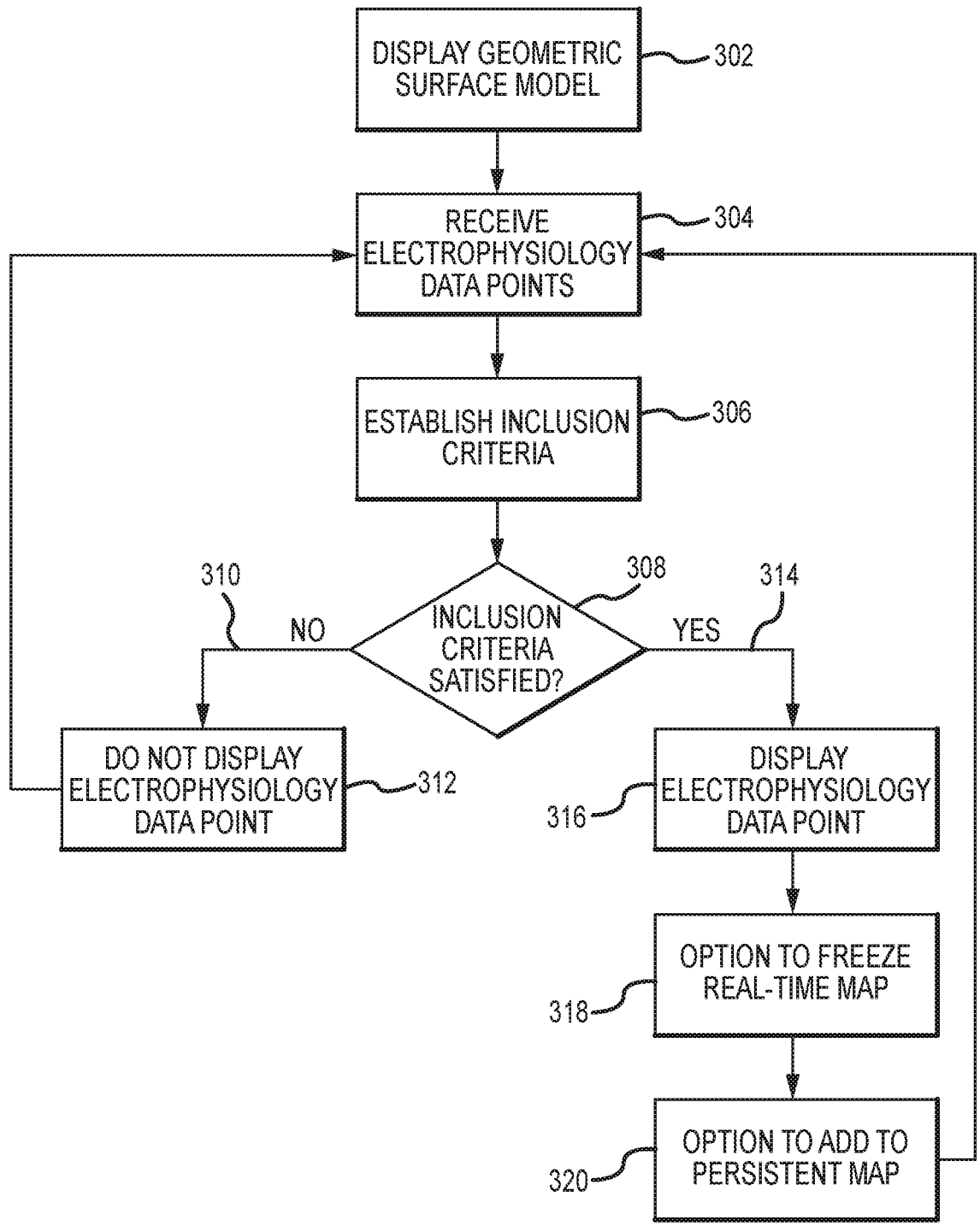
FIG. 3 is a flowchart of representative steps that can be carried out to generate an electrophysiology map according to various aspects disclosed herein.

Various aspects of the instant disclosure will now be described with reference to FIGS. 3-6. FIG. 3 is a flowchart depicting representative steps of an exemplary method 300 for generating a real-time electrophysiology map according to the instant disclosure. In some embodiments, for example, FIG. 3 may represent several exemplary steps that can be carried out by the computer 20 of FIG. 1 (e.g., by one or more processors 28 executing one or more specialized modules, such as an electrophysiology mapping processor executing an electrophysiology mapping module as further described below).

Figure 4:
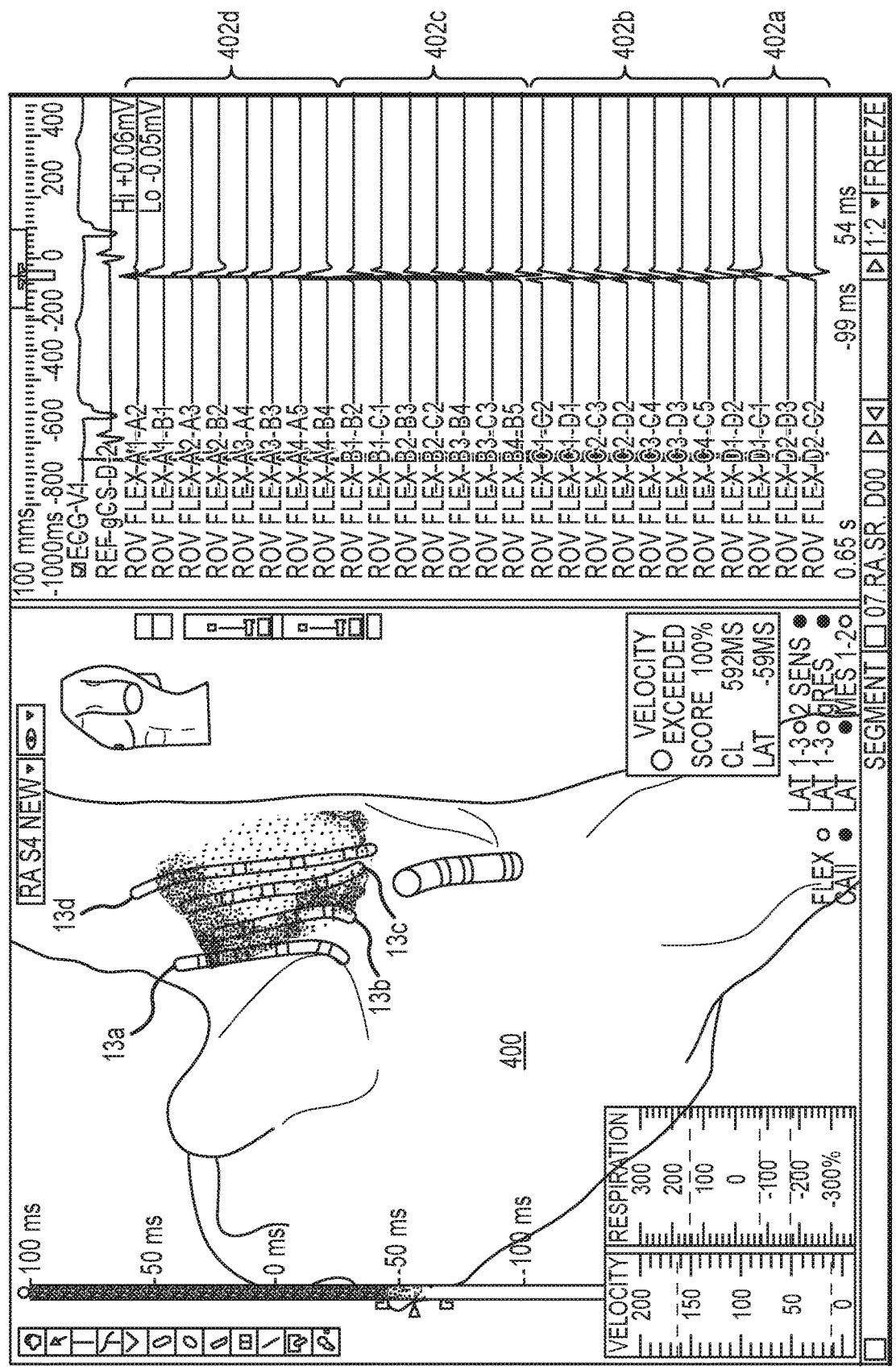
FIGS. 4-6 are representative real-time electrophysiology maps according to the teachings herein.
Figure 5:
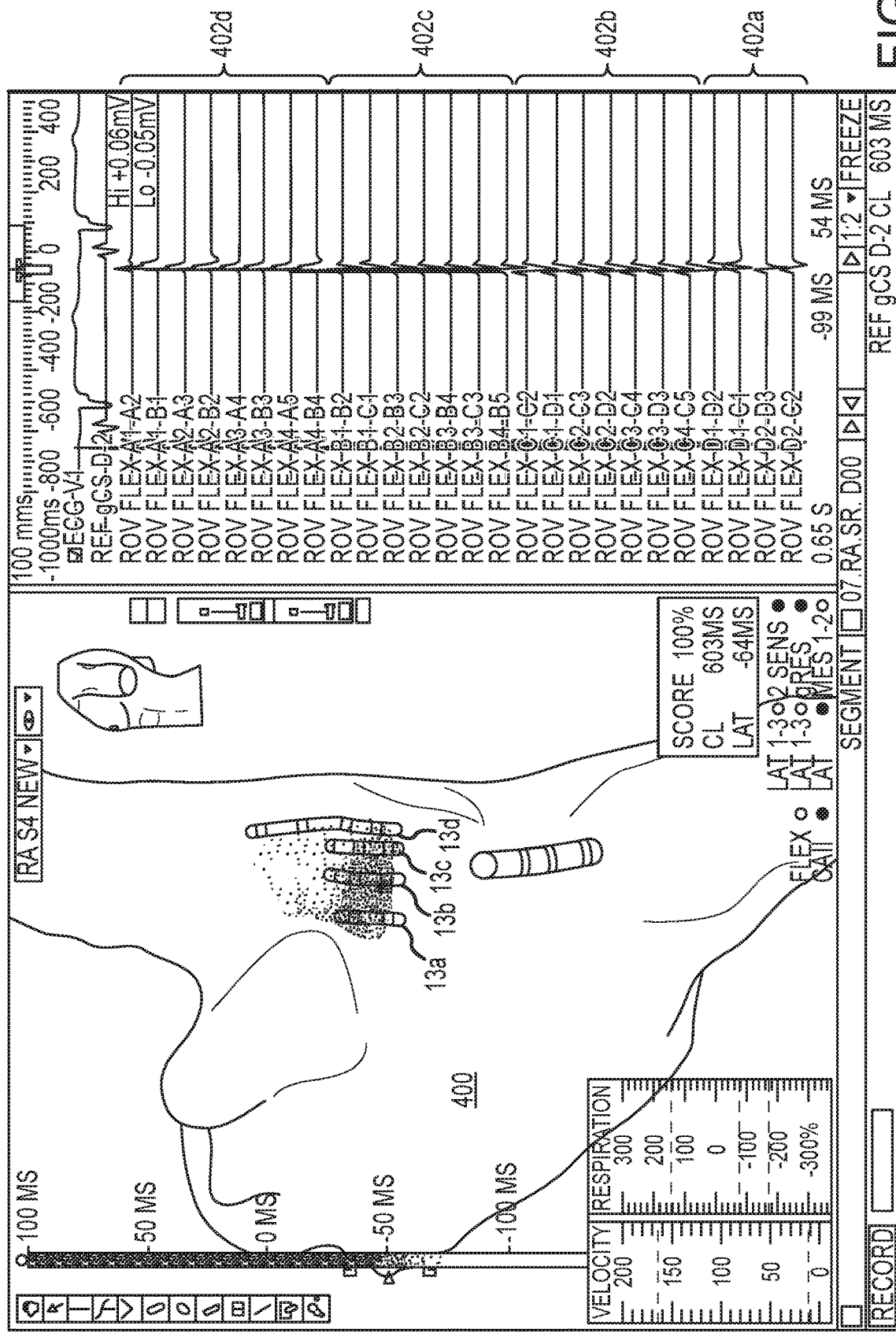
Figure 6:
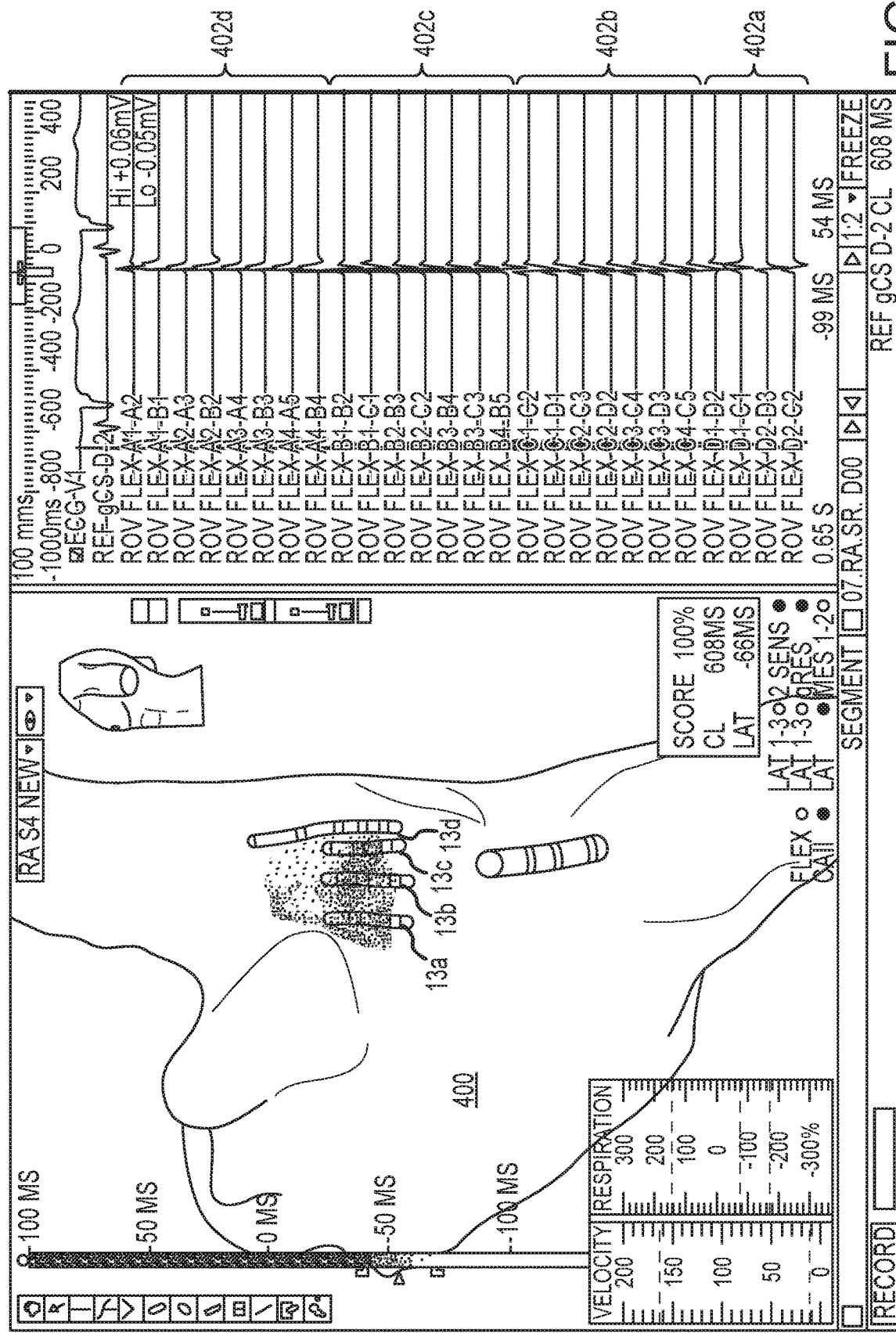

FIGS. 4-6 depict exemplary electrophysiology maps generated using various aspects disclosed herein and data collected and processed utilizing localization system 8 (e.g., using computer system 20).

It should be understood that the teachings herein can be software- and/or hardware-implemented, and that they may be executed on a single CPU, which may have one or more threads, or distributed across multiple CPUs, each of which may have one or more threads, in a parallel processing environment.

In block 302 of FIG. 3, a geometric surface model of a portion of a patient's heart is displayed. Those of ordinary skill in the art will be familiar with numerous ways to acquire and display a suitable geometric surface model, such as by using localization system 8 to gather a cloud of geometry points to which a surface is fit.

In block 304, a plurality of electrophysiology data points are received using a plurality of intracardiac electrodes, such as electrode 17, 52, 54, or 56 on catheter 13. As discussed above, each electrophysiology data point includes both measured electrophysiology data (e.g., an EGM) and measured location data. The ordinarily skilled artisan will appreciate that both electrophysiology data and location data can be continuously measured. Thus, for purposes of this disclosure, the term "receiving an electrophysiology data point" means associating measured electrophysiology data and measured location data as an electrophysiology data point for analysis and processing. "Receiving" does not, however, require that the electrophysiology data point be "saved" such that it becomes part of a persistent electrophysiology map (although it may be "stored" in the sense of being retained in volatile and/or non-volatile memory included, for example, within computer system 20). Indeed, in certain aspects of the disclosure, an electrophysiology data point is received and analyzed, and the results of the analysis (e.g., peak-to-peak voltage, activation time, average cycle length, conduction velocity, fractionation index, and the like) are optionally displayed and then discarded from the displayed electrophysiology map during the next cardiac cycle (or other time interval) when a new electrophysiology data point is received. In embodiments where the received electrophysiology data point is also "saved" as part of a persistent electrophysiology map, this disclosure will explicitly so state.

Steps 302 and 304 are illustrated to good advantage in FIG. 4. The left-hand pane of FIG. 4 depicts a geometric surface model 400 of the right atrium (for purposes of illustrating the teachings herein, a swine heart was used to generate FIGS. 4-6). The right-hand pane of FIG. 4 depicts a plurality of EGMs measured by electrodes carried by a multi-spline intracardiac catheter. The catheter splines, depictions of which are shown along with surface model 400 in the left-hand pane, are designated 13a, 13b, 13c, and 13d; their corresponding EGMs are designated 402a, 402b, 402c, and 402d (the plurality of electrodes on each catheter spline 13a, 13b, 13c, and 13d, though depicted in the left-hand pane of FIG. 4, are not separately numbered in order to avoid obscuring the drawing).

In block 306, one or more inclusion criteria are established. The inclusion criteria are used to determine whether a received electrophysiology data point should be displayed on a real-time electrophysiology map.

One contemplated inclusion criterion is a projection distance criterion that checks the projection distance from the measured location data for a received electrophysiology data point to the reconstructed surface of the heart against a preset projection distance threshold. The projection distance criterion is satisfied when the projection distance does not exceed the projection distance threshold.

One suitable way to determine the projection distance between a received electrophysiology data point and the reconstructed surface is to compute the shortest distance between the measured location data for the electrophysiology data point and the geometric surface model of the patient's heart. The projection distance threshold can be user adjustable and can, in certain embodiments, can be between about 5 mm and about 15 mm.

Contact force between catheter splines 13a, 13b, 13c, 13d and the tissue is another suitable inclusion criterion. A contact force inclusion criterion can be satisfied if the contact force exceeds a preset contact force threshold.

Another suitable inclusion criterion is electrical coupling between the electrodes on catheter splines 13a, 13b, 13c, 13d and the tissue. In some embodiments, an electrical coupling inclusion criterion can be satisfied if a measurement of electrical coupling between the tissue and one or more electrodes exceeds a preset threshold. In other embodiments, the electrical coupling inclusion criterion can be based upon a rate of change in electrical coupling between the tissue and one or more electrodes.

In some cases, such as for certain types of atrial fibrillations, the cycle length of the underlying condition may be considered regular and relatively organized, and thus can be easily synchronized with a reference signal, such as a signal from a fixed reference electrode. In other cases, however, the cycle length may be irregular and relatively disorganized, making it difficult to synchronize the electrophysiology data points dynamically using such a signal. In such circumstances, cycle length may be used as an inclusion criteria for triggering the inclusion of one or multiple electrophysiology data points. In one such embodiment, for example, a minimum cycle length threshold (e.g., about 280 ms) may be set to trigger the inclusion of electrophysiology data points based on the presence of relatively fast rotors (e.g., a rotor having a cycle length of about 340 ms). The threshold value may be either preset or can be user selected (e.g., as a value input to computer 20).

Still other inclusion criteria, such as stability and speed, are described in U.S. patent application publication no. 2012/0029504, which is hereby incorporated by reference as though fully set forth herein.

It is also contemplated that the one or more inclusion criteria can be applied in various combinations. For example, a composite inclusion criterion can require satisfaction of both a projection distance criterion and an electrical coupling criterion.

Decision block 308 checks whether the one or more inclusion criteria established in block 306 are satisfied. If not (e.g., the projection distance exceeds the projection distance threshold) (path 310), then the measured electrophysiology data is not depicted on the geometric surface model (block 312). If, on the other hand, the inclusion criteria are satisfied (e.g., the projection distance does not exceed the projection distance threshold) (path 314), then the measured electrophysiology data is depicted on the geometric surface model (block 316) in real-time (that is, it is immediately displayed). Thus, as shown in FIG. 4, measured electrophysiology data for several of the electrodes carried by catheter splines 13a, 13b, 13c, and 13d that satisfy the inclusion criteria can be depicted in color on surface model 400 proximate catheter splines 13a, 13b, 13c, and 13d.

Following either path 310/block 312 or path 314/block 316, the process can repeat from block 304 with a new plurality of subsequently-received electrophysiology data points. For example, the process can be repeated from time interval to time interval, such as from heartbeat to heartbeat. FIG. 5 depicts a representative electrophysiology map taken in the right atrium at a later time than is shown in FIG. 4, after catheter splines 13a, 13b, 13c, and 13d have moved to a new location. Similarly, FIG. 6 depicts a later time than is shown in FIG. 5, but with catheter splines 13a, 13b, 13c, and 13d in the same general position.

Stated another way, the teachings herein allow the most currently-measured electrophysiology data from any number of intracardiac electrodes to be depicted in an electrophysiology map, provided that they satisfy the established inclusion criteria. If desired, only the most current electrophysiology data can be depicted in the electrophysiology map, with previously-measured electrophysiology data hidden or removed from the depiction, such that the electrophysiology map is updated or refreshed in real-time.

It is also contemplated, however, that older electrophysiology data can remain displayed on the electrophysiology map. This can be useful, for example, in allowing a practitioner to "draw" an electrophysiology map for a region by moving catheter 13 into locations where no measured electrophysiology data is yet depicted. For example, as catheter splines 13a, 13b, 13c, and 13d change position from FIG. 4 to FIG. 5, the graphical representation of measured electrophysiology data shown in FIG. 4 could remain, with the graphical representation of measured electrophysiology data shown in FIG. 5 being an addition thereto rather than a replacement thereof. In such embodiments, it may also be desirable to gate the receipt of electrophysiology data points (for example, to signals from ECG 6, though various gating techniques will be familiar to those of ordinary skill in the art) in order to ensure that electrophysiology data points received later in the procedure are at least at the same phase in the cardiac cycle as those received earlier in the procedure.

As described above, one trigger for receiving new electrophysiology data points is the passage of time. In some embodiments, the practitioner can select a specified time interval to refresh the electrophysiology map with then-current measured electrophysiology data. For example, the practitioner could specify that the map should be refreshed at one second intervals.

In other embodiments, the time interval is triggered by some other event, such as a particular point in the cardiac cycle (for example, by gating the receipt of electrophysiology data points to signals from ECG 6).

As described above, all received electrophysiology data points can be "stored," in the sense of being added to volatile and/or non-volatile memory (e.g., RAM and/or a hard drive) that is part of computer system 20, for example for future analysis. In addition, however, in block 318, the practitioner can also be provided the option to "freeze" the real-time electrophysiology map (that is, to render the graphical representation static) and, if desired, to add the electrophysiology data points depicted in the now-static electrophysiology map to a persistent electrophysiology map; this process is referred to herein as "saving" the electrophysiology data points (block 320). Electrophysiology data points can also be saved automatically, for example whenever the inclusion criteria are satisfied, or as disclosed in U.S. application Ser. No. 14/462,128, filed 18 Aug. 2014 and incorporated by reference as though fully set forth herein.

In certain aspects, the real-time electrophysiology map can be augmented with a persistent electrophysiology map generated from a plurality of previously-saved electrophysiology data points. That is, both real-time and previously-saved electrophysiology data points can be represented on the same surface model. In order to facilitate distinguishing between the two data sets, the real-time electrophysiology data points can be presented using one drawing convention, and the previously-saved electrophysiology data points can be presented using a different drawing convention.

Figure 7:
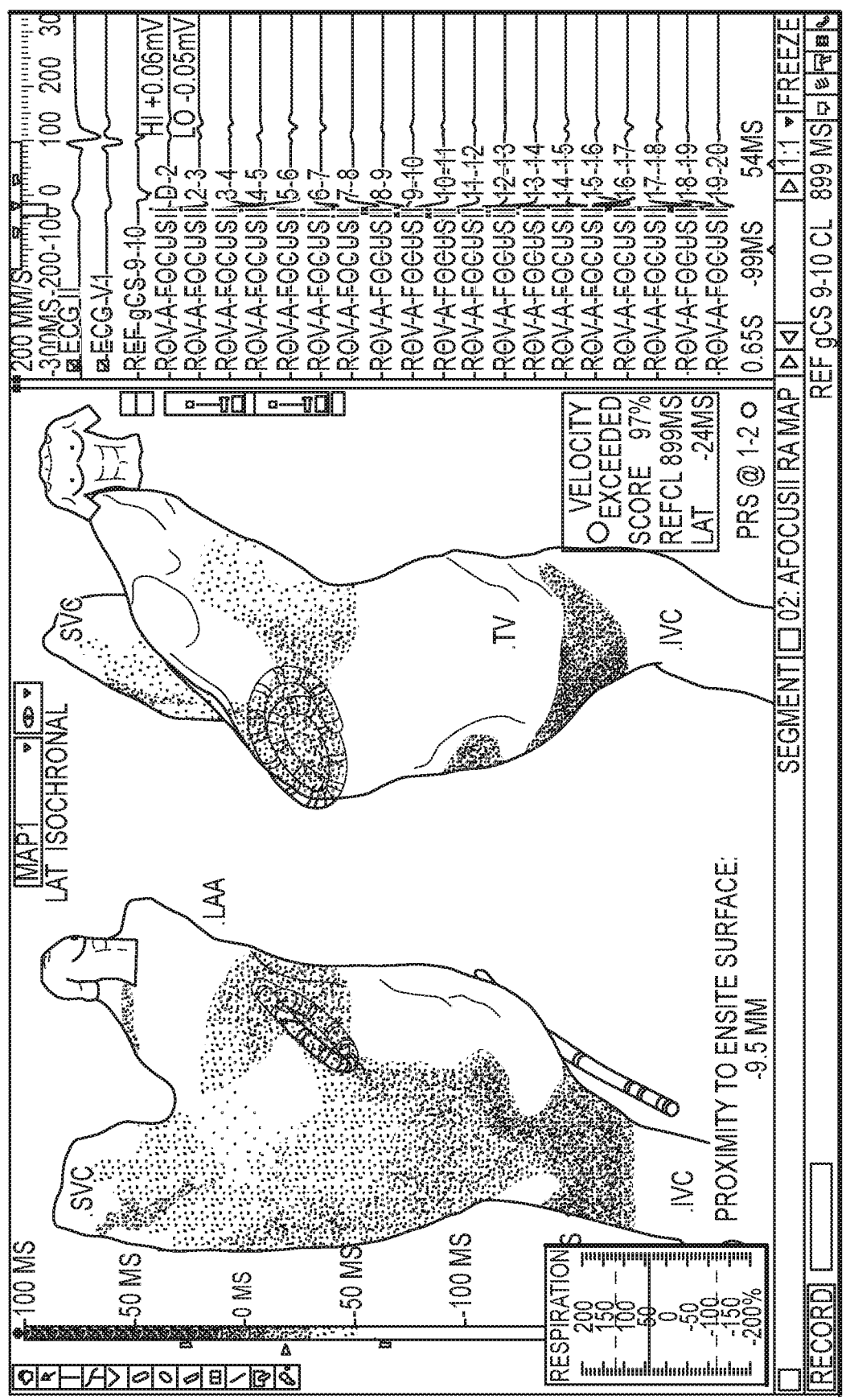
FIGS. 7-9 are representative combined real-time and persistent electrophysiology maps according to the teachings herein.
Figure 8:
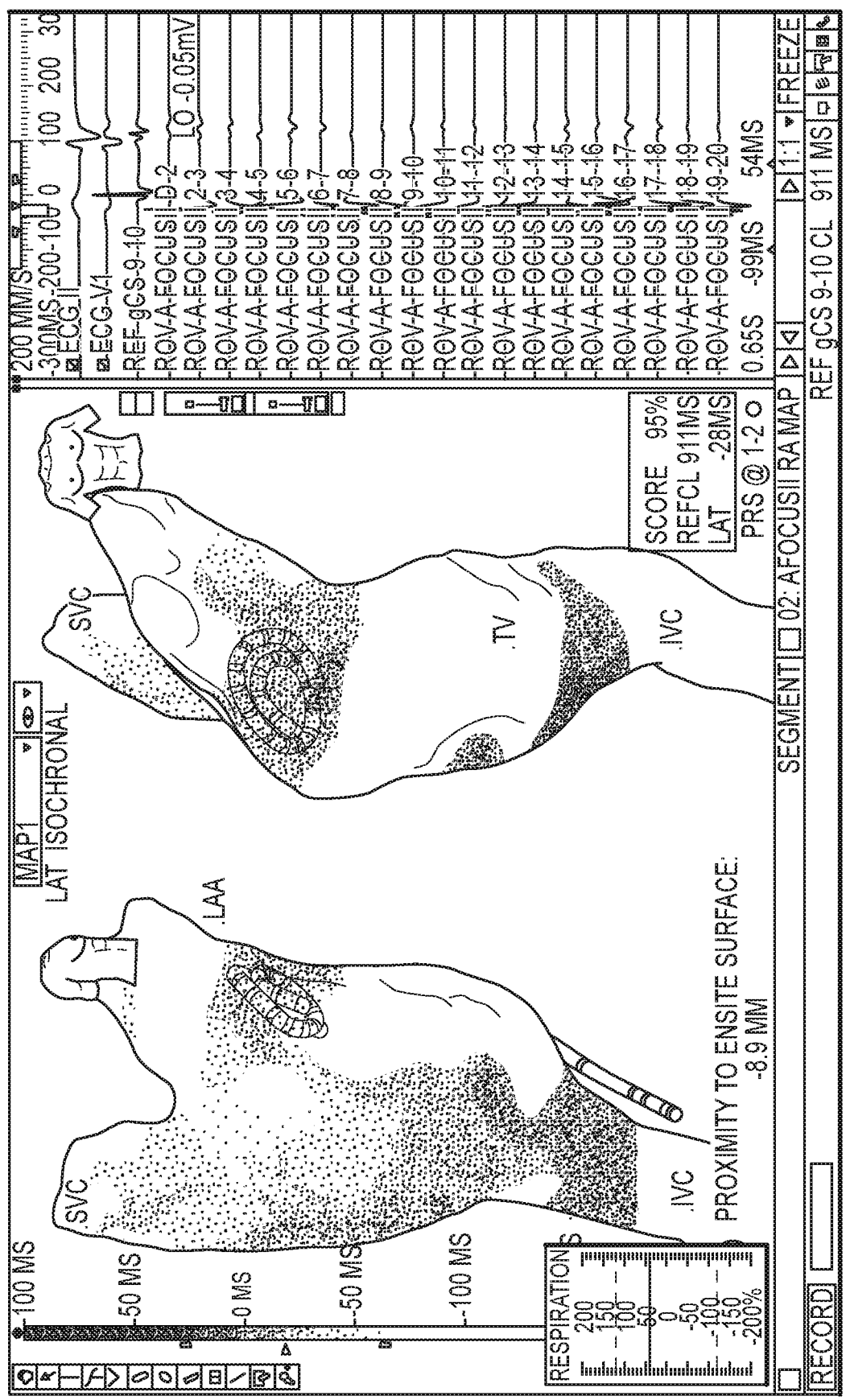
Figure 9:
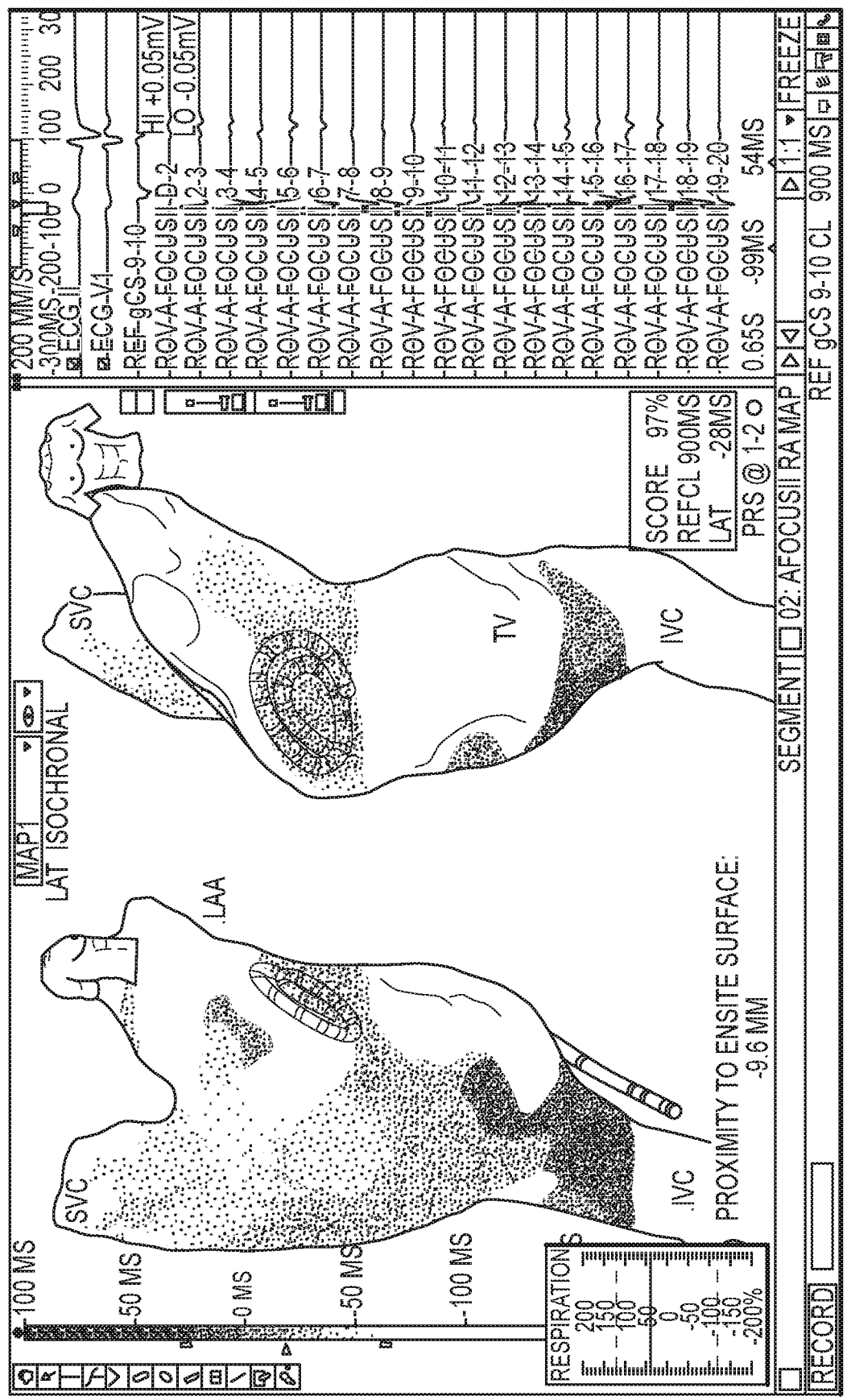

Various suitable drawing conventions that can be used to display multiple variables or data sets are described in U.S. provisional application No. 62/063,989, filed 15 Oct. 2014, which is hereby incorporated by reference as though fully set forth herein. As one example, FIG. 7-9 show, over a series of cardiac cycles, a combined real-time and persistent electrophysiology map where the electrophysiology data points from the persistent map are shown in yellow and the real-time electrophysiology data points are shown in red. Alternatively, previously-saved electrophysiology data can be shown with a different transparency and/or at a different intensity than the real-time electrophysiology data.

In addition, the real-time electrophysiology data, if added to a persistent electrophysiology map, can be used to update electrophysiology data within the persistent map having a common location. For example, the real-time data can overwrite previous electrophysiology data at the common location. Alternatively, the real-time data can be used to refine previous electrophysiology data, for example by averaging the previous and real-time data at the common location. For purposes of this disclosure, locations can be considered "common" if they are coincident in real-space. Further, for purposes of this disclosure, locations are "coincident in real-space" if they are within the error tolerance for the measurement of locations by system 8 or within the minimum separation of points on the geometric surface model.

With respect to the foregoing disclosure, the ordinarily skilled artisan will be familiar with various techniques that can be used to generate a graphical representation of electrophysiology data on a surface model (that is, an electrophysiology map). The ordinarily skilled artisan will also be familiar with various settings associated with the generation of an electrophysiology map from one or more electrophysiology data points, including reference electrograms or artificial trigger, roving electrograms, map type, detection method and settings, color high, color low, interpolation distance, interior projection, exterior projection, and the like. The electrophysiology maps described herein can also be updated as the user adjusts these settings. That is, the electrophysiology maps described herein can be refreshed in real time not only to reflect the most currently-received electrophysiology data, but also to reflect the most current user-defined display settings.

Although several embodiments of this invention have been described above with a certain degree of particularity, those skilled in the art could make numerous alterations to the disclosed embodiments without departing from the spirit or scope of this invention.

For example, by viewing a real-time electrophysiology map according to the teachings herein, a practitioner receives an indication of the spatial relationship between each electrode (e.g., 17, 52, 54, 56) on a multi-electrode catheter (e.g., 13) and the cardiac surface, because measured electrophysiology data will only display if the electrode is sufficiently close to the cardiac surface, in sufficient contact with the cardiac surface, and/or sufficiently electrically coupled to the cardiac surface. In response, the practitioner can reorient and/or reposition the medical device before carrying out a diagnostic or therapeutic procedure.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system for generating a real-time electrophysiology map of a portion of a patient's heart, comprising:
   a surface modeling processor configured to display a model of a surface of the portion of the patient's heart; and
   an electrophysiology mapping processor configured to:
      receive, as input, a plurality of electrophysiology data points, each electrophysiology data point of the plurality of electrophysiology data points comprising measured electrophysiology data and measured location data;
      display, in real-time on the model of the surface of the patient's heart, the measured electrophysiology data for each electrophysiology data point of the plurality of electrophysiology data points when and only when a distance between the measured location data for the electrophysiology data point to the surface of the patient's heart falls below a preset projection threshold.

2. The system according to claim 1, wherein the electrophysiology mapping processor is further configured to save one or more electrophysiology data points of the plurality of electrophysiology data points to a plurality of saved electrophysiology data points.

3. The system according to claim 2, wherein the electrophysiology mapping processor is further configured to update one or more previously-saved electrophysiology data points when saving the one or more electrophysiology data points to the plurality of saved electrophysiology data points.

4. The system according to claim 2, wherein the electrophysiology mapping processor is further configured to overwrite one or more previously-saved electrophysiology data points when saving the one or more electrophysiology data points to the plurality of saved electrophysiology data points.

5. The system according to claim 1, wherein the electrophysiology mapping processor is further configured to display a plurality of saved electrophysiology data points on the model of the surface of the patient's heart.

6. The system according to claim 5, wherein the display, in real-time on the model of the surface of the patient's heart, of the measured electrophysiology data uses a first display convention and the display of the plurality of saved electrophysiology data points on the model of the surface of the patient's heart uses a second display convention different from the first display convention.

7. The system according to claim 1, wherein the electrophysiology mapping processor is configured to
   receive, as input, the plurality of electrophysiology data points; and
   display, in real-time on the model of the surface of the patient's heart, the measured electrophysiology data for each electrophysiology data point of the plurality of electrophysiology data points when and only when a distance between the measured location data for the electrophysiology data point to the surface of the patient's heart falls below a preset projection threshold according to a preset time interval.

8. The system according to claim 7, wherein the preset time interval is user-selectable.

9. The system according to claim 7, wherein the electrophysiology mapping processor is configured to display, in real-time on the model of the surface of the patient's heart, only measured electrophysiology data from a current time interval.

10. The system according to claim 1, wherein the electrophysiology mapping processor is configured to
    receive, as input, the plurality of electrophysiology data points; and
    display, in real-time on the model of the surface of the patient's heart, the measured electrophysiology data for each electrophysiology data point of the plurality of electrophysiology data points when and only when a distance between the measured location data for the electrophysiology data point to the surface of the patient's heart falls below a preset projection threshold when a preset triggering event occurs.

11. The system according to claim 10, wherein the preset triggering event is a point in the cardiac cycle.

12. The system according to claim 11, wherein the preset triggering event is user-selectable.

13. The system according to claim 10, wherein the electrophysiology mapping processor is configured to display, in real-time on the model of the surface of the patient's heart, only measured electrophysiology data from a current triggering event.

14. A system for generating a real-time electrophysiology map of an anatomical region, comprising:
    an electrophysiology mapping processor configured to:
       receive, as input, a plurality of electrophysiology data points, each electrophysiology data point of the plurality of electrophysiology data points comprising measured electrophysiology data and measured location data; and for each received electrophysiology data point of the plurality of received electrophysiology data points:
determine a distance from the measured location data to a surface of the anatomical region and
graphically represent the measured electrophysiology data on a model of the surface of the anatomical region in real-time when and only when the distance from the measured location data to the surface of the anatomical region falls below a preset projection threshold.

15. The system according to claim 14, wherein the electrophysiology mapping processor is further configured to save the received plurality of electrophysiology data points to an electrophysiology map.

16. The system according to claim 14, wherein the electrophysiology mapping processor is configured to receive, as input, the plurality of electrophysiology data points according to a preset time interval.

17. The system according to claim 14, wherein the electrophysiology mapping processor is configured to receive, as input, the plurality of electrophysiology data points when and only when a preset triggering event occurs.

* * * * *